(12) United States Patent
Ruchala et al.

(10) Patent No.: US 6,618,467 B1
(45) Date of Patent: Sep. 9, 2003

(54) MEGAVOLTAGE COMPUTED TOMOGRAPHY DURING RADIOTHERAPY

(75) Inventors: Kenneth J. Ruchala, Madison, WI (US); Gustavo H. Olivera, Madison, WI (US); Thomas R. Mackie, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/913,084

(22) PCT Filed: Mar. 29, 2000

(86) PCT No.: PCT/US00/08291

§ 371 (c)(1),
(2), (4) Date: Aug. 9, 2001

(87) PCT Pub. No.: WO00/59576

PCT Pub. Date: Oct. 12, 2000

Related U.S. Application Data

(60) Provisional application No. 60/127,630, filed on Apr. 2, 1999.

(51) Int. Cl.[7] .................................................. A61N 5/10
(52) U.S. Cl. .............................. 378/65; 378/4; 378/62; 378/147
(58) Field of Search ................................ 378/65, 4, 21, 378/62, 150, 147, 151, 152, 153

(56) References Cited

U.S. PATENT DOCUMENTS

| | | | |
|---|---|---|---|
| 4,442,489 A | 4/1984 | Wager | 364/414 |
| 5,396,889 A | 3/1995 | Ueda et al. | 127/653.1 |
| 5,724,400 A | * 3/1998 | Swerdloff et al. | 378/150 |

FOREIGN PATENT DOCUMENTS

| | | |
|---|---|---|
| EP | 0 205 720 | 12/1986 |
| EP | 0 382 560 | 8/1990 |

OTHER PUBLICATIONS

International Search Report, PCT/ISA/210, under date of mailing of Jul. 27, 2000 in connection with Int'l Application PCT/US00/08291.

\* cited by examiner

*Primary Examiner*—Drew A. Dunn
*Assistant Examiner*—Courtney Thomas
(74) *Attorney, Agent, or Firm*—Quarles & Brady LLP

(57) ABSTRACT

Reduced dose megavoltage CT images are obtained using low flux data resulting from leakage through modulating shutters and/or collected by other means and augmented by incomplete high flux data collected during radiation therapy. The ability to construct tomographic projection sets from significantly varying flux rate data is provided by the use of air scans windowed to account for variations in mechanical leaf movement. These methods are also provide a means of imaging the patient entirely during radiation therapy treatments without any additional scan time.

17 Claims, 5 Drawing Sheets

MEGAVOLTAGE COMPUTED TOMOGRAPHY DURING RADIOTHERAPY

This application claims the benefit of provisional application No. 60/127,630 filed Apr. 2, 1999.

This invention was made with United States government support awarded by the following agencies: NIH CA 48902. The United States has certain rights in this invention.

BACKGROUND OF THE INVENTION

In external radiation therapy, converging beams of radiation are used to irradiate cancerous tissue within a patient.

Tomotherapy is a form of external radiation therapy in which the radiation source is placed on a gantry rotating in a single plane about an axis through the patient. The patient may be translated across the plane during the rotation to impart a relative helical motion between the patient and a point on the gantry. During this rotation, the radiation beam is modulated by a multi-leaf collimator (MLC) or other modulating device which divides the radiation beam into independently controllable rays. By controlling the intensity of each ray as a function of gantry angle, radiation dose may be precisely placed in arbitrary cross-sectional regions within the body. Methods of constructing and of operating such tomotherapy equipment are described in U.S. Pat. No. 5,317,616 issued May 31, 1994 entitled Method and Apparatus for Radiation Therapy, and U.S. Pat. No. 5,548,627 issued Aug. 20, 1996 entitled Radiation Therapy System With Constrained Rotational Freedom as assigned to the assignees of the present application and hereby incorporated by reference.

Tomotherapy's ability to precisely place a radiation dose makes it important to be able to accurately image the treatment region and precisely locate the patient during treatment. U.S. Pat. No. 5,724,400 issued Mar. 3, 1998 entitled Radiation Therapy System With Constrained Rotational Freedom also assigned to the assignees of the present invention and hereby incorporated by reference describes a combination computed tomography (CT) machine and radiation tomotherapy machine that can provide both imaging and accurate registration of the patient.

In CT, a planar beam of kilovolt energy x-rays are projected through the patient at a variety of gantry angles much like that done with tomotherapy but without modulation of the beam rays by an MLC. Bodily structures attenuate the rays and this attenuation is detected by a detector. A cross-sectional image may be reconstructed from "projections" of attenuation data of rays at each gantry angle over a range of gantry angles that define a "tomographic projection set". The tomographic projections set typically includes rays spanning the entire width of the patient over at least 180° of gantry angles. Reconstructing an image from less than a tomographic projection set can cause severe image artifacts obscuring essential body structure.

While normally CT uses kilovoltage x-rays having much lower energy than those used in radiation therapy, it is known that images can be constructed using the same megavoltage x-rays used in radiation therapy. In this way the need for a separate kilovoltage x-ray source is avoided. Megavoltage images have the further advantage of better representing the actual absorption of the body structures of radiation at the megavoltage lever thus making those images superior for treatment planning and dose verification. U.S. Pat. No. 5,673,300 issued Sep. 30, 1997 entitled Method of Registering A Radiation Treatment Plan To A Patient teaches methods of using a detector with megavoltage x-rays to verify patient location and for dose evaluation. These patents are also incorporated by reference.

Nevertheless, the use of megavoltage x-rays for the generation of a CT image (MVCT) has some disadvantages. First, the requirement that a complete tomographic projection set be obtained normally requires a pre-scanning of the patient before radiation therapy. This pre-scanning process increases the total time of the treatment and entails the possibility of patient movement between the scan and therapy. Pre-scanning typically forgoes the ability to use the MVCT images for real-time correction or verifications. Finally, high contrast MVCT over the required tomographic projection set significantly increases the dose to the patient.

BRIEF SUMMARY OF THE INVENTION

The present invention eliminates or reduces the amount of additional time required to take an MVCT scan and/or minimizes the additional dose required by MVCT by collecting at least a portion of the CT data during the radiation therapy. The problem of image artifacts resulting from the inevitably incomplete projections provided by the modulated radiation therapy radiation, is overcome by supplementing this "high flux" radiation therapy data with low flux data obtained separately either in a pre-scan or during the radiation therapy. A tomographic projections set is formed of mixed low and high flux data.

Using low flux data minimizes the extra radiation to the patient required for MVCT whereas the high noise inherent in using low flux data is substantially corrected by the high flux data obtained from the therapy. Alternatively in certain situations, the low flux data alone may be used.

Specifically then, the present invention provides a combination radiation therapy and tomographic imaging machine having a megavoltage radiation source directing a radiation beam formed of rays directed generally along an axis. A gantry holds the radiation source to rotate the angle of the axis about a treatment volume and a radiation detector is positioned on the gantry across the treatment volume opposite the radiation source to provide data of a projection. A modulator is positioned between the radiation source and the treatment volume to modulate the flux of the rays.

An electronic computer communicating with the modulator controls the modulator to direct selected high flux rays at selected axis angles at the patient within the treatment volume according to a radiation treatment plan. The selected rays and angles comprise less than the tomographic projection set and thus produce a high flux, incomplete tomographic projection set. Low flux rays are also directed at the patient within the treatment volume to acquire low flux data. The low flux data is combined with the high flux incomplete tomographic projection set to produce an augmented but complete tomographic projection set which may be reconstructed into an image.

Thus, it is one object of the invention to employ radiation used in radiation therapy for CT imaging even though it is seriously incomplete for tomographic purposes. The low flux data augments the incomplete high flux radiation therapy data to provide a tomographic image without overly increasing the total dose to the patient.

The low flux data that is collected may be a complete tomographic projection set or may be an incomplete tomographic projection set.

Thus it is another object of the invention to provide great flexibility in acquisition of the low flux data.

In one embodiment, the modulator is a multi-leaf collimator having multiple leaves that may be opened or closed to pass or occlude rays and the low flux data are obtained from leakage through the leaves when they are closed.

Thus it is another object of the invention to provide a simple method of producing low flux data in a radiation therapy machine.

The leaves may be open for a proportion of time during increments of axis angle according to the radiation treatment plan to produce the high flux incomplete tomographic projection set and the electronic computer may execute the stored program to position the proportion of time in the open state after the beginning of each angular increment so that the low flux data may be collected at the beginning of each angular increment.

Thus it is another object of the invention to provide a ready means of obtaining a complete tomographic projections set of low flux data at regular intervals during the radiation therapy itself.

Alternatively, the low flux rays may be obtained by opening the leaves to pass rays not required by the radiation treatment plan.

Thus it is another object of the invention to provide a means of obtaining a complete tomographic projections set of low flux data.

The electronic computer may execute the stored program to center the proportion of time the leaves are in the open state within each angular increment and the low flux data may be collected at the center of each angular increment. Alternatively, or in addition, the computer may optimize the pattern of opening and closing the leaves according to the radiation treatment plan, presupposing an opening of leaves necessary to generate the low flux data.

Thus, it is another object of the invention to obtain tomographic projection set data at times where the greatest amount of flux associated with radiation therapy occurs so that a complete projection can be obtained with the least additional dose.

The electronic computer may further operate to control the modulator to direct selected high flux rays at selected axis angles at the treatment volume without the patient according to the radiation treatment plan to acquire a normalizing high flux incomplete tomographic projection set ("high flux air-scan") and to direct low flux rays at the treatment volume without the patient to acquire normalizing low flux data from the radiation detector ("low flux air scan"). Prior to combining the high flux incomplete tomographic projection set and the low flux data to produce the augmented tomographic projection set, the high flux incomplete tomographic projection set may be normalized with the normalizing high flux incomplete tomographic projection and the low flux data may be normalized with the normalizing low flux data.

Thus it is another object of the invention to better accommodate data of widely varying flux rates into a single tomographic projection scan without introducing extreme artifacts. The air scans provide common units of attenuation that may be combined between high and low flux data. When the modulator includes leaves, as described above, which may move between states to occlude and pass given rays where at any given time, a leaf may be stationary or moving and the data acquired from the radiation detector for reconstruction may be obtained only at times when the leaves are stationary.

Thus it is another object of the invention to provide a method of obtaining repeatable air scans and conventional scans using an MLC as is necessary for the combination of high and low flux data. The inventors have determined that sufficient repeatability can obtained using mechanical MLC through this windowing process.

The foregoing and other objects and advantages of the invention will appear from the following description. In this description, reference is made to the accompanying drawings, which form a part hereof, and in which there is shown by way of illustration, a preferred embodiment of the invention. Such embodiments and their particular objects and advantages do not define the scope of the invention, however, and reference must be made therefore to the claims for interpreting the scope of the invention.

DETAILED DESCRIPTION OF THE INVENTION

Figure 1:
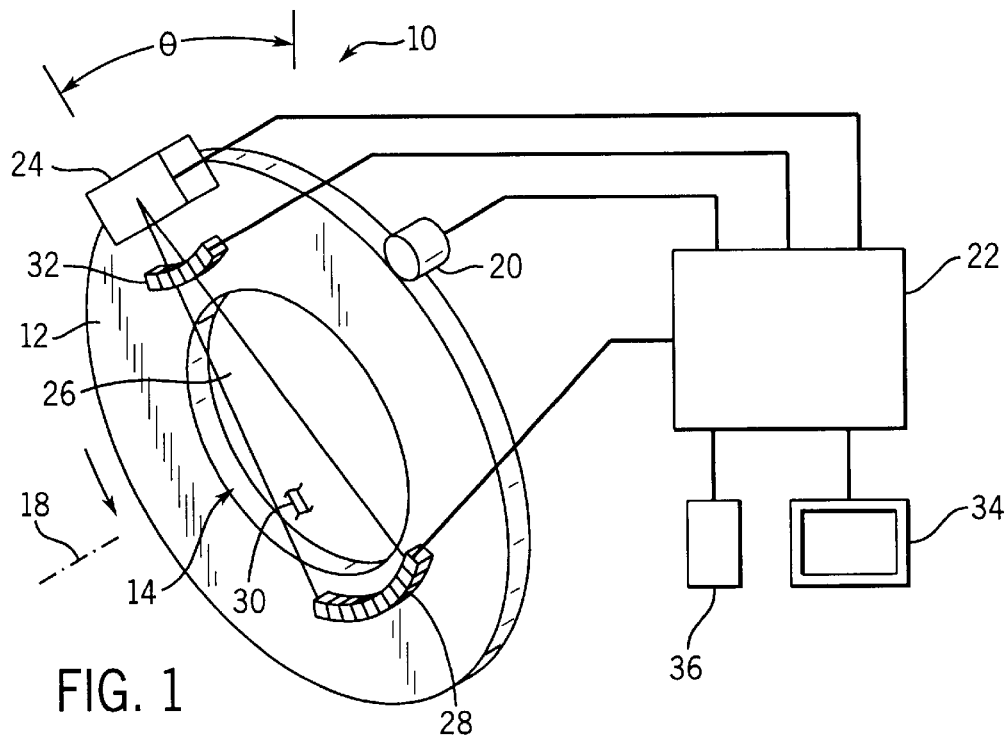
FIG. 1 is a simplified perspective view of a tomotherapy machine suitable for use with the present invention providing a controllable radiation source producing a radiation beam, a multi-leaf collimator, and a detector for rotation on a gantry under control of a computer.

Referring now to FIG. 1, a tomotherapy CT machine 10 per the present invention provides an annular gantry 12 having a central bore 14 for receiving a patient and patient support (not shown). The gantry is rotatable about a central bore axis 18 by actuator 20 communicating with a central computer 22. The actuator 20 receives signals from the computer 22 to control rotation of the gantry 12 and transmits to the computer 22 position information.

A megavoltage x-ray source 24, such as a linac, is mounted at one end of a diameter of the gantry 12 to project a beam 26 of x-rays along the diameter across the opening of the bore 14 to a detector 28. The detector 28 includes a number of elements providing separate measurements of the beam 26 along ones of a set of rays 30. The detector 28 transmits the measurements of the ray's intensities to the computer 22.

The x-ray source 24 may be controlled by the computer 22 both to turn it on and off and to change its flux rate by controlling a pulse rate as is understood in the art. Positioned between the x-ray source 24 and the bore 14 is a multi-leaf collimator 32 that allows individual control of the average fluence of the rays 30.

The computer 22 may include a display 34 and an entry device 36 such as a keyboard or the like and may be a dedicated part of the tomotherapy machine 10 or may be implemented offline or may be a combination of both as will be understood in the art.

Figure 2:
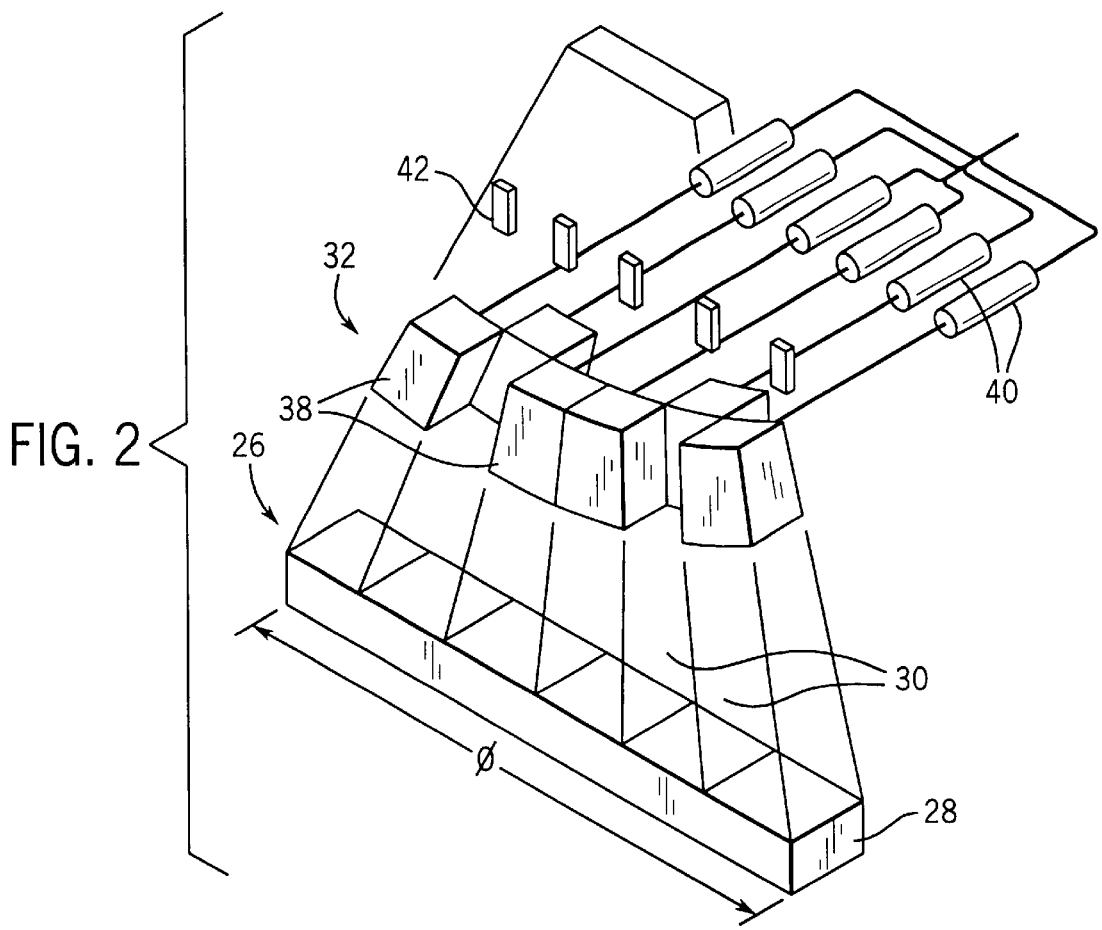
FIG. 2 is a perspective view of the multi-leaf collimator of the present invention showing movement of leaves in and out of the radiation beam according to the control of the computer.

Referring now to FIG. 2, the multi-leaf collimator 32 in a preferred embodiment includes a number of radio-opaque leaves 38 that each subtends an angle of one ray 30 of the beam 26 as may be received by the detector 28. "Radio opaque" as used herein and as understood in the art refers to a gross characterization of the leaves 38, however, like all physical materials they in fact do allow some leakage of x-rays through them.

The leaves 38 are attached to an actuator mechanism 40 which may move the leaves axially in and out of the beam 26 so that individual rays 30 are occluded or passed. Sensors 42 may provide a signal confirming the position of the leaves 38.

By controlling the duty cycle of the leaves in the beam 26, that is, the proportion of time which they are occluding individual rays 30 or passing individual rays 30 during a given interval, the average flux of the rays 30 may be controlled within a continuous range. This duty cycle modulation is well known in the art and is described in the patents cited above, hereby incorporated by reference.

Figure 3:
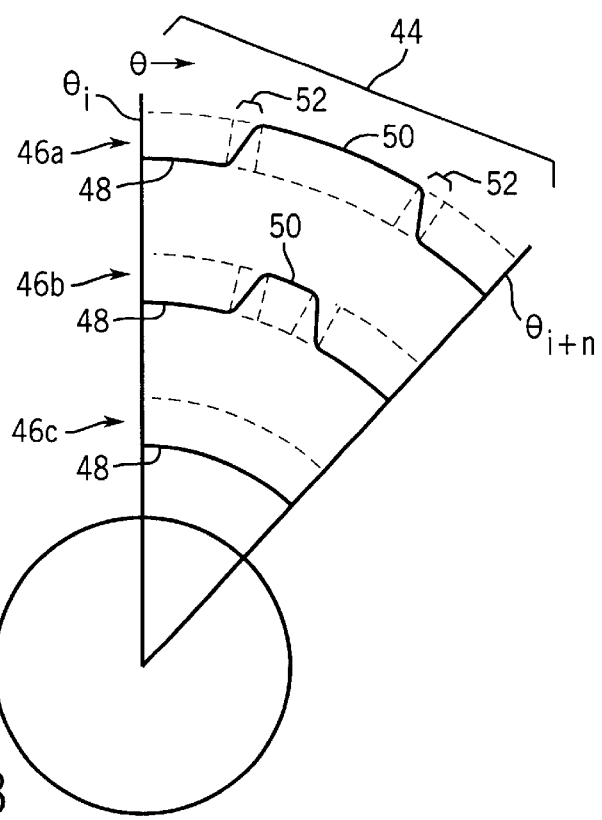
FIG. 3 is a polar graphical representation in expanded angular scale of motion of the leaves in and out of the beam for three leaves showing a centering of the opening of the leaves within the angular increment.
Figure 14:
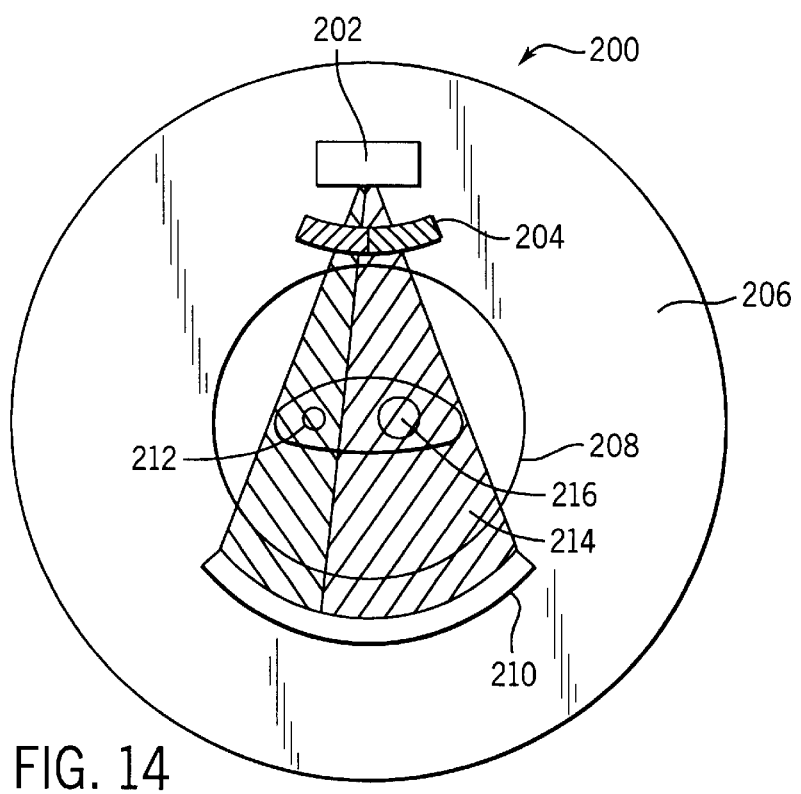
FIG. 14 is a simplified elevational view of a CT machine such as may use principles of the present invention to provide reduced dose in areas outside of a region of imaging interests.

Referring now to FIGS. 1 and 3, for purposes of tomotherapy, the gantry 12 may be rotated about the axis 18 to project radiation toward the patient at a variety of angles θ. Angular rotation may be divided into a series of discrete angular intervals 44 ($\theta_i$) shown greatly enlarged in FIG. 3. Each angular interval 44 defines the base over which the duty cycle of the leaves is modulated. For example, for 50% flux modulation at $\theta_i$, the leaf 38 will be closed one-half of the time that it takes the gantry 12 to move through the angular interval 44.

It is desirable that the opening of adjacent leaves 38 be coordinated to occur with the maximum amount of overlap so that effects such as caused by the attenuation of the x-rays rays around edges of closed leaves 38 and shadowing of leaf support structure, such as tongue-and-groove elements that may be used to support the leaves (not shown), can be minimized. Further it is desirable to center the opening time of the leaves 38 within the angular interval 44 so as to produce a dose pattern that is symmetric about the center of each angular interval 44 for simplicity in treatment planning.

In FIG. 3, the states 46a–c of three leaves 38 are shown as a function of angular position θ for one angular interval 44. The states 46a and 46b begin the angular interval 44 in closed positions 48 and move to open positions 50 (of different durations) centered within the angular interval 44. A transition period 52 occurs between the closed position 48 and open position 50 and conversely between the open position 50 and closed position 48 for both of the states 46a and 46b. State 46c, in contrast, remains closed during the entire angular interval 44. It will be understood that the state 46a having the greatest proportion of open time provides the highest average flux, having a higher duty cycle than state 46b, which in turn has a higher average flux that state 46c.

The transition periods 52 may be estimated based on measurements of the operation of the multi-leaf collimator 32 or may be detected by use of the sensors 42 or by monitoring transitions of the signals received by the detector 28 or a variety of other means. The detection of leaf position may make use of the techniques taught in U.S. Pat. No. 5,394,452 issued Feb. 28, 1995 entitled Verification System For Radiation Therapy assigned to the same assignee as the present invention and hereby incorporated by reference.

Figure 4:
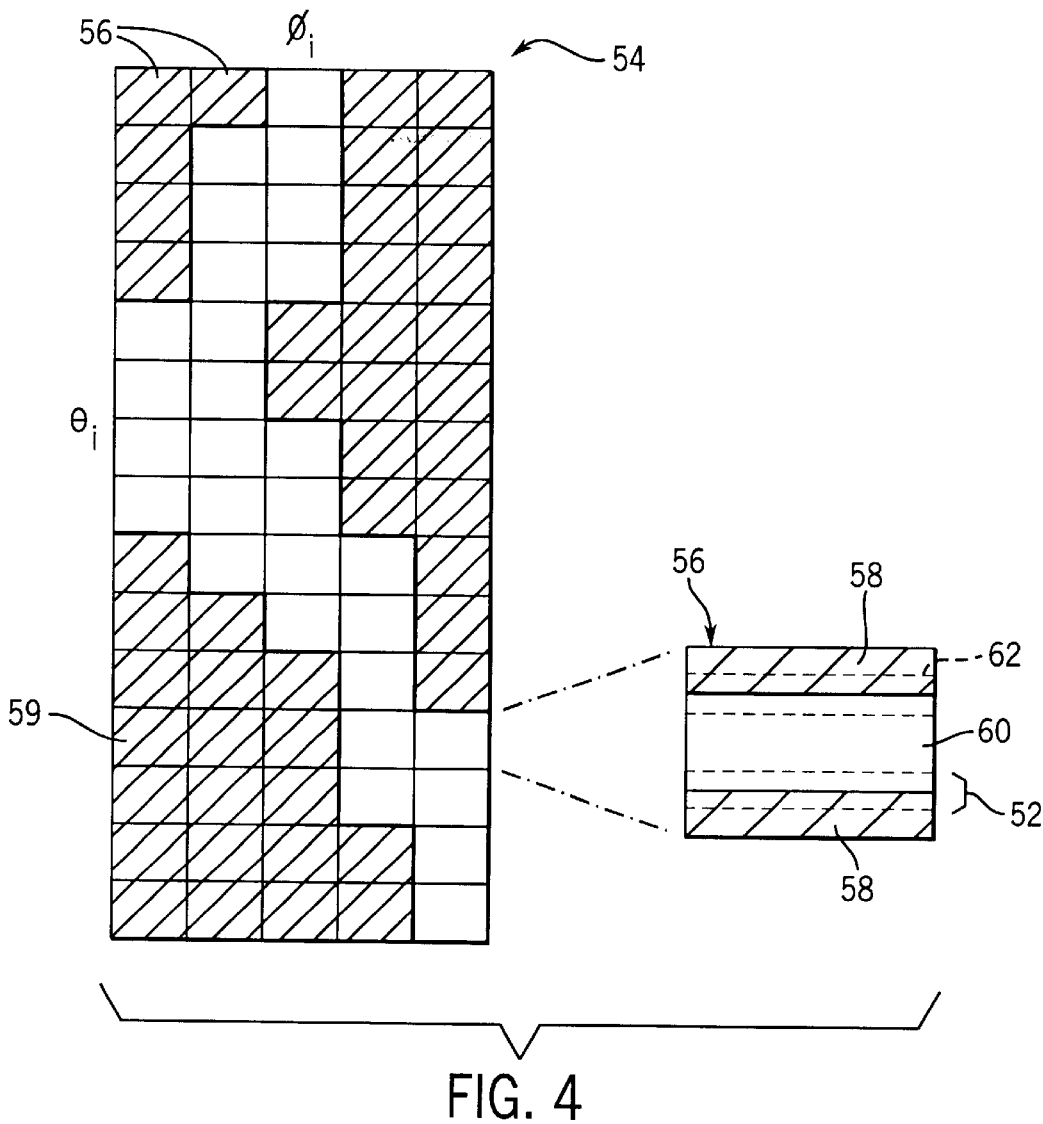
FIG. 4 is a simplified graphical representation of a sinogram for controlling the motion of the leaves in accordance with a radiation treatment plan for different angular increments of FIG. 3 showing an expanded form, the opening and closing of one leaf for one angular increment of the sinogram, and showing in dotted lines periods of transition of the leaves between open and closed states.

Referring to FIG. 4, a determination of the duty cycle of each leaf 38 designated by variable $\phi_i$ for each angular interval $\theta_i$ may be described by a sinogram 54 as is understood in the art. Each element 56 of a row of the sinogram 54 indicates the duty cycle or average flux modulation for each leaf $\phi_i$ at a given gantry angle whereas the columns indicate different angular intervals $\theta_i$ in the angle of the gantry. A number of methods of determining the sinograms for particular radiation treatment plans are known in the art and are described in the predecessor patents cited above.

The present invention contemplates but does not require that the gantry 12 will maintain continuous rotation during the radiation therapy. With such continuous rotation, a θ offset within a column corresponds generally with time and accordingly, each element 56 may show the actual time modulation pattern of the corresponding leaf 38 where cross-hatched, leaf-closed areas 58 show leaf closures and blank leaf open areas 60 showing leaf openings. The duty cycle will be the leaf open area 60 divided by the entire duration of the angular interval 44. Dotted lines show the boundaries 62 of the transition periods 52 straddling the interface between leaf open areas 60 and leaf-closed areas 58.

The present inventors have recognized that the transition periods 52 are highly variable for practical mechanical systems. This variability may be accommodated in radiation therapy by measuring the actual radiation delivered with transition periods 52 and compensating for those variations in later radiation treatments. This variability, however, interferes with the combination of high and low flux data because it prevents accurate isolation of the amount of attenuation caused by the patient from what appears to be attenuation but is in fact shutter variation.

Accordingly, the present invention "windows" the sinogram 54 to find regions of the sinogram where it can be expected that the leaves will not be in a state of movement or that motion will be negligible. Thus within windowed regions of the sinogram, the transmitted flux through the patient should be identical for repeated measurements.

Figure 5:
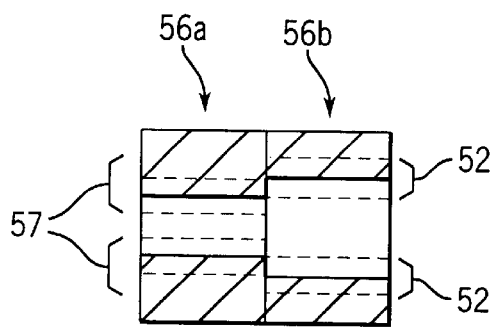
FIG. 5 is a figure similar to the expanded form of FIG. 4 showing the opening and closing of two adjacent leaves during a given angular increment and the periods of leaf motion and the production of a "windowed" sinogram indicating acceptable periods for data acquisition only during times when all leaves have ceased motion.
Figure 6:
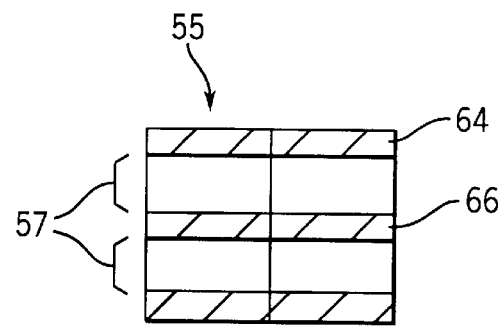
FIG. 6. is a figure showing the locations of the windowed low flux and high flux data.

Referring to FIGS. 5 and 6, generation of the windowed sinogram 55 considers an entire row 6f the sinogram 54 (shown in FIG. 5) as variations in some leaves 38 will affect the received radiation along rays 30 of adjacent leaves 38 through scatter and refraction. In an alternative embodiment, the windowing process considers less than the entire row of the sinogram 54 but only elements 56 that are within a predetermined distance of varying leaves 38 and thus whose rays 30 are likely to be affected by scatter from the rays of the varying leaves 38. Two elements 56a and 56b are shown. In a first step of generation of the windowed sinogram, the transition periods 52 for each element 56a and 56b are combined to create a row-wide transition region 57 being the union in time (and gantry angle) of all transition periods 52 of all elements 56a and 56b of the row. The row wide transition region 57 covers the transition periods 52 of all elements 56 of that row. This row-wide transition region 57 is then applied to each element 56a and 56b to define a windowed leaf-closed region 64, being a subset of leaf-closed areas 58 outside of the row-wide transition region 57, and define as a windowed open region 66 being a subset of leaf open areas 60 outside of the row-wide transition region 57.

Henceforth, it will be understood that when data is collected from the detector 28, it is collected from regions 64 if data is to be collected with the leaf 38 closed and from regions 66 if the data is to be collected when the leaf 38 is open. In this way reproducible data may be collected as will be used as described below.

Referring again to FIG. 4, and as mentioned above, reconstruction of a tomographic image requires that a tomographic projection set be collected corresponding generally to the dimensions of the sinogram 54. Thus, at a plurality of angles $\theta_i$, in the simplest case spanning 360°, a projection including each of the rays $\phi_i$ must be collected. Failure to collect a complete tomographic projection set can result in image artifacts that may obscure not only regions through which the rays are not collected pass, but also regions outside of these areas where data has been collected.

A typical sinogram 54, however, will have extensive regions 59 (indicated by cross hatching) where the treatment plan requires that no radiation be transmitted. Thus if the radiation passing open leaves 38 alone is used for tomographic reconstruction, insufficient data will be acquired.

Figure 7:
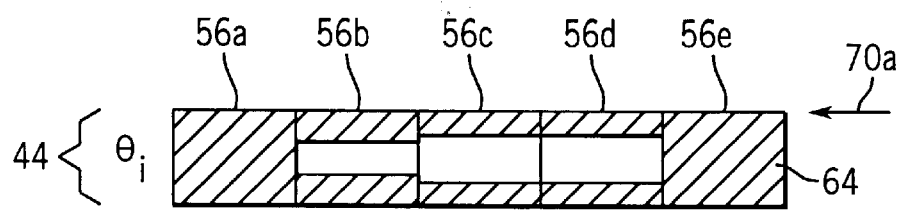
FIG. 7 is a simplified representation of a single example row of the sinogram of FIG. 4, as windowed, showing a location of data acquisition to obtain low flux data in a first embodiment of the invention.

Referring now to FIG. 7, an example sinogram row is shown having elements 56a through 56e where elements 56a and 56e correspond to leaf closures such as would block the corresponding rays 30 necessary to complete a projection of a tomographic projection set. The present inventors have recognized that even though a projection cannot be obtained from rays through open leaves 38, that the leaves 38, rather than being perfectly opaque, in fact allow some leakage radiation to pass and that this leakage radiation is sufficient to obtain a tomographic projection set. Most simply, the tomographic data may be obtained at time 70a being a beginning of angular interval 44 that defines the row $\theta_i$. The data is collected only out of the windowed leaf-closed areas 64 as described above. The data is reproducible from scan to scan. Further because all the leaves 38 are closed at the beginning of each angular interval 44, according to the preferred embodiment of leaf control, a full tomographic projection set is readily obtained at regular gantry angles during the radiation therapy.

Because such data is collected from rays 30 passing through closed leaves 38 and thus that are low in flux, the collection of data does not unduly increase the dose received by the patient in the radiotherapy. The low flux rays produce an image with low signal-to-noise ratio, but the present inventors have determined that such an image is adequate for many tasks of imaging high contrast structures within the body.

Figure 8:
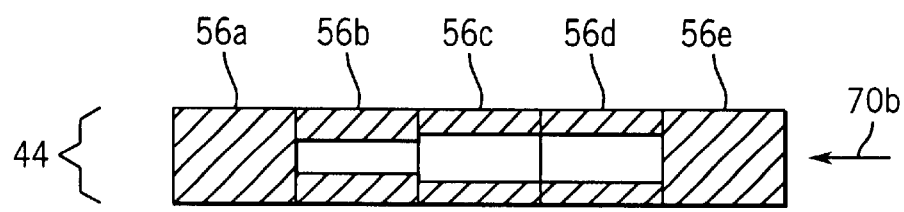
FIG. 8 is a figure similar to that of FIG. 7 showing a second location for obtaining mixed low and high flux data according to a second embodiment of the invention.

Referring now to FIG. 8, in a second embodiment, this low flux data can be augmented by high flux data produced by, for example, open leaves 56b through 56d which are in fact open during the interval 44. In this case too, the low flux data collected need not be a complete tomographic projection set so long as it may be augmented by high flux data to fill in those missing elements. As shown in FIG. 8 at a sampling time 70b at the middle of angular interval 44, low flux data may be obtained through elements 56a and 56e to be supplemented by high flux data obtained through elements 56b through 56d. By placing the sampling interval 70b in the center of interval 44, the greatest probability exists of open leaves to augment that data.

The combination of the low flux data and the high flux data will be described below.

A combination of the low flux data and high flux data is made possible by converting them first to attenuation values through the use of "air scans" as will be described below. Generally, for each row of the sinogram 54, a measurement of radiation through air, without the patient in place, is made during the windowed periods and this measurement is compared to a measurement for the same row with the patient in place. Attenuations for each element 56a through 56e are calculated and used to provide the basis for the tomographic projection set. In this way, attenuation provides a common unit for the combination of high and low flux data. Use of only the windowed periods of the pattern of FIG. 8 for both the air scan and the actual scan allows this comparison to be made with an acceptable degree of accuracy.

Each of the techniques of FIGS. 7–8 may be performed during the radiation therapy itself. Thus there is no penalty in lengthening the treatment time for using these imaging techniques. Further, the techniques of FIGS. 7 and 8 do not increase the dose to the patient.

Figure 9:
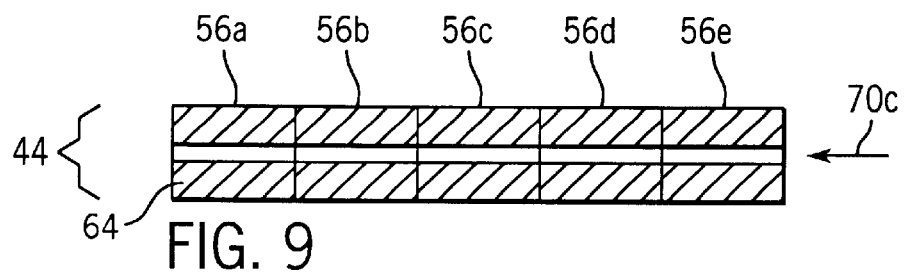
FIG. 9 is a figure similar to that of FIGS. 7 and 8 showing a third embodiment where low flux data is obtained by a brief opening and closing of all leaves.

Referring now to FIG. 9 in an alternative embodiment, a pretreatment scan may be provided in which the leaves 38 while normally closed may be briefly opened for each of elements 56a–56e at regular angular intervals. The time of opening may be controlled to provide for the desired low flux data at sampling interval 70c for an entire tomographic projections set which may be reconstructed directly or augmented with high flux data taken during the radiation therapy as will be described below.

Figure 10:
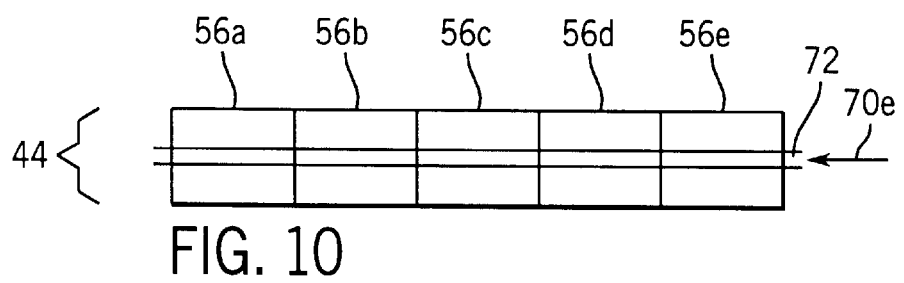
FIG. 10 is a figure similar to that of FIGS. 7–9 showing a method of obtaining low flux data by opening all leaves and precisely controlling the emission of radiation from the radiation source per a fourth embodiment.

Referring now to FIG. 10 in an alternative embodiment, the leaves 56a through 56e are kept open and the linac is pulsed or otherwise gated during activation period 72 to provide for a collection of a complete low dose tomographic projection set at sampling interval 70e to be used as described above.

Figure 11:
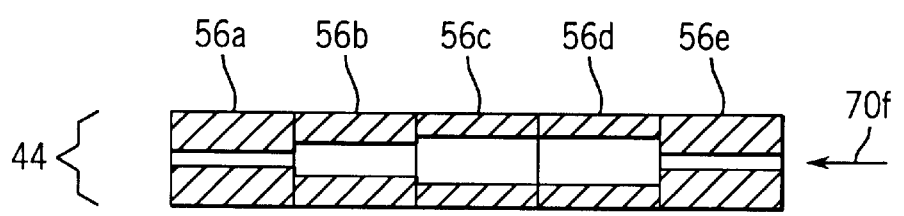
FIG. 11 is a figure similar to that of FIGS. 7–10 showing a method of obtaining low flux data in a fifth embodiment briefly opening only leaves otherwise closed during radiation therapy.

Finally referring to FIG. 11, the techniques of FIG. 9 and FIG. 8 may be combined with data collected at interval 70f centered within the interval 44 and leaves 56a and 56e (normally closed by operation of the sinogram) may be overridden to provide for brief openings of those leaves at the center of interval 44. This technique will be necessary if additional generations of multi-leaf collimators provide greater radio opacity preventing sufficient leakage for the generation of tomographic images, and the image quality is generally superior for non-leakage data.

While images may be reconstructed wholly from the low flux data collected by the techniques of FIG. 7, FIG. 9 and FIG. 10, an important aspect of the present invention is that it allows the radiation therapy radiation to be used to significantly improve the signal-to-noise ratio of the tomographic image produced by low flux data. In this way, the benefits of low additional dose and high signal noise ratio images may both be achieved.

Figure 12:
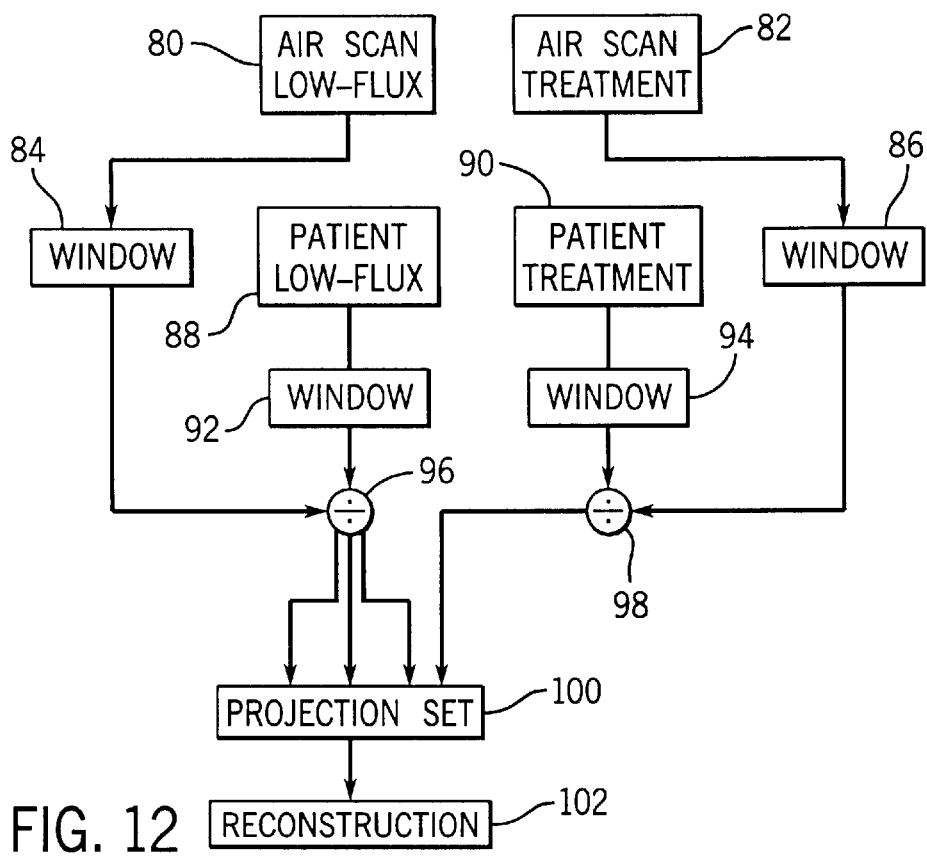
FIG. 12 is a flow diagram showing acquisition of data in various scans of the patient as may be used in the present invention in which low flux data is augmented by high-flux data obtained during the radiation therapy.

Referring now to FIG. 12, this process of augmentation of the low flux data begins with a low flux air scan 80 and high flux air scan 82, the former being the collection of the low flux data described above with respect to FIGS. 7 through 11 and the latter being a collection of high flux data incident to the radiation therapy. It will recognized in certain instances, the low flux air scan 80 and high flux air scan 82 can carried out simultaneously, for example, per the techniques described with respect to FIGS. 7, 8, and 11, and in other cases the low flux air scan 80 and high flux air scan 82 will occur at different times within a single scan or within different scans entirely.

Critical to the ability to use these air scans however, is that data is collected only during the windowed portions of the sinogram patterns as described above with respect to FIG. 5. This process of selecting the windowed periods is shown by process block 84 which provides a windowing of the low flux air scan 80 and process block 86 providing a windowing of the data of the high flux air scan 82.

The patient is then placed in position and patient low flux data is obtained at process block 88 and patient high flux or treatment data is obtained at process block 90. The same sinograms used in low flux air scan 80 and high flux air scan 82 are used in process blocks 88 and 90 and their consistency is ensured by windowing 92 operating on the data collected at process block 88 and windowing 94 operating on the data collected at process block 90.

At logarithmic attenuation block 96, the data from process blocks 84 and 92 are compared to obtain attenuation values according to the well-known formula:

$$\lambda(x) = -\ln\left(\frac{\Phi_i(x)}{\Phi_0(x)}\right)$$

where $\lambda(x)$ is attenuation at a given element 56 and $\Phi_o$ is corresponding air scan data and $\Phi_i$ is corresponding patient scan data.

The attenuation values from process block 96 which may or may not represent a complete low flux tomographic projection set can be combined with selected or all attenuation values of the high flux data from process block 98 to form tomographic projection set at process block 100. In the case where there are multiple attenuation values for a given element of the sinogram (and hence the tomographic projections set) the elements may be averaged together after being weighted by flux. It is also possible to use some low flux tomographic projection sets without the addition of high flux data.

The augmented tomographic projection set is then reconstructed according to well-known techniques at process block 102 such as filtered backprojection. In this way, the low flux data is combined with high flux radiation treatment data to significantly improve the signal to noise ratio of the reconstructed data.

In a further embodiment, the low flux data may also be augmented by other low flux data collected at various points during the scan following the pattern of process blocks 82, 90, 86, 94, and 98 as applied to that low flux data. The process blocks of FIG. 12 will generally further include standard tomographic correction techniques of normalizing the detector 28, beam hardening corrections and the like. The present invention may be used with partial scan techniques.

Figure 13:
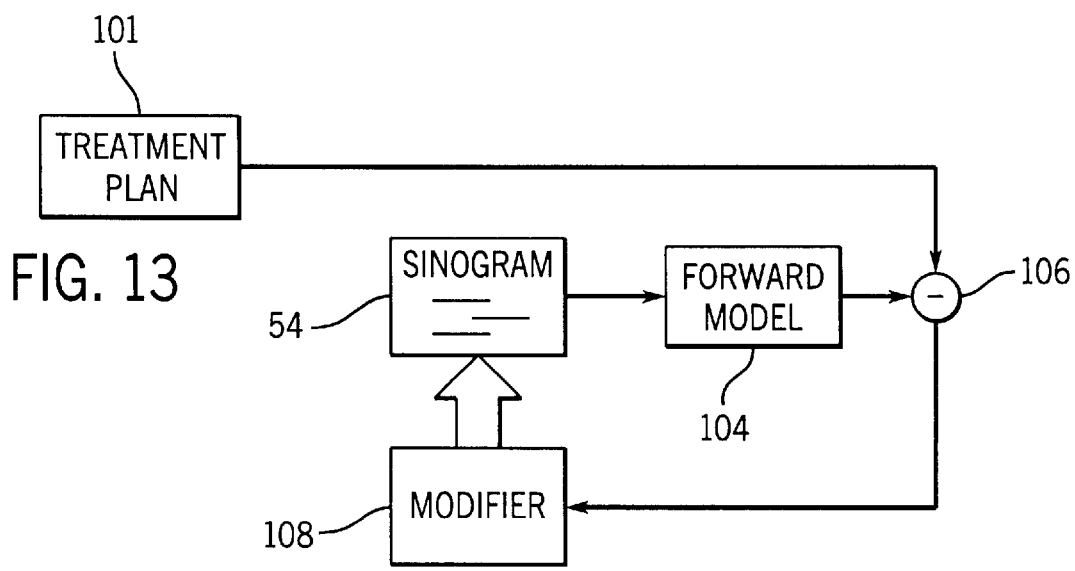
FIG. 13 is a flow diagram of a method of obtaining a sinogram of FIG. 4 from a radiation treatment plan by incorporating leaf movement necessary to obtain the low flux data in the sinogram optimization process.

Referring now to FIG. 13, in the case where additional data collection is added to the radiation treatment plan to obtain the low flux data as shown in FIGS. 9 through 11, for example, this flux may be integrated in the optimization process used to produce the sinogram 54 from a radiation treatment plan 101 to reduce their effect on increasing the total dose.

As shown in FIG. 13, a typical radiation treatment planning process will involve generation of a radiation treatment plan 101 by a physician, describing generally desired doses at different regions of the patient. An initial sinogram 54 obtained by well-known approximation or other techniques may then be provided to a forward model 104 which computes the dose that would be provided to a patient by that sinogram. The forward model may include a tomographic image of the patient to determine attenuation coefficients.

This computed dose from the forward model 104 is compared to the dose of the radiation treatment plan 101 at comparison block 106 and used to drive a modification algorithm 108 which changes the sinogram 54 in a way calculated to improve the match between its dose and that of the radiation treatment plan 101. In a modification to this generalized process, well known in the art, the sinogram 54 may have certain leaves locked open for example by programming the modification algorithm 108 that these leaves cannot be changed. The locked leaves can correspond to the leaves that must be open (per the technique of FIG. 11, for example) for producing the low flux data for tomographic imaging. By locking these leaves and applying the forward model 104 iteratively, some of the necessary openings of the leaves for tomography may be incorporated into the actual radiation treatment plan or may be compensated for in other leaf openings at later portions in the plan thus minimizing the additional dose if any needed by the tomographic imaging.

In working with the present invention, the inventors have noted that in images obtained for radiation treatment plans which center high flux radiation only at certain location within the patient, that the combination of low flux data from rays directed at locations outside the region of interest of the patient and high flux data typically toward the region of interest of the patient provides good quality imaging of the region of interest without significant artifacts despite the absence of a high flux (uniformly low signal-to-noise ratio) tomographic projection set.

This suggests a technique of conventional CT imaging in which a CT dose is dynamically controlled to reduce the dose in regions of the patient where image quality is not as important. It will be remembered that generally dose cannot be completely eliminated in off region of interest areas because of artifacts that are introduced that may extend into the region of interest.

Accordingly, a CT machine 200 can be constructed having a conventional kilovoltage x-ray tube 202 followed by a multi-leaf collimator 204 or another methodology to modulate the beam possibly providing lower resolution than that used by the tomotherapy machine described above. Per conventional practice, both the tube 202 and collimator 204 are mounted on a rotatable gantry 206. Opposite a bore 208 of the gantry is a CT detector 210.

Such a CT system uses the multi-leaf collimator 204 to reduce but not eliminate flux in low interest region 212, are provide higher flux in high interest region 214 about a structure of interest 216. The exact regions 212 and 214 will change with angular rotation of the gantry 206 as tracked by the collimator 204 using a sinogram-type control strategy. Finally, the low flux and high data combine as shown in FIG. 12 to produce a resulting image with reduced dose.

In cases where the region of interest is centered near the axis of rotation of the gantry 206, the multi-leaf collimator can be replaced with a fixed filter providing the desired attenuation pattern. Such a CT machine may, for example, be useful with pediatric patients.

It will be recognized that this invention is not limited to a particular multi-leaf collimator design but can be used in any radiotherapy system in which the flux of individual rays may be controlled and in which a tomographic projection set may thus be collected.

It is specifically intended that the present invention not be limited to the embodiments and illustrations contained herein, but modified forms of those embodiments including portions of the embodiments and combinations of elements of different embodiments as come within the scope of the following claims.

We claim:

1. A combination radiation therapy and tomographic imaging machine comprising:

a megavoltage radiation source directing a radiation beam formed of rays directed generally along an axis;

a gantry holding the radiation source to rotate the angle of the axis about a treatment volume;

a radiation detector positioned on the gantry across the treatment volume opposite the radiation source to receive and measure radiation of the rays to provide data of a projection;

a modulator modulating the flux of the rays passing through the treatment volume;

an electronic computer executing a stored program to:
   (i) control the modulator to direct selected high flux rays at selected axis angles at the patient within the treatment volume according to a radiation treatment plan, the selected rays and angles comprising less than a tomographic projection set, to acquire a high flux incomplete tomographic projection set from the radiation detector;
   (ii) direct low flux rays at the patient within the treatment volume to acquire low flux data from the radiation detector;
   (iii) combine the high flux incomplete tomographic projection set and the low flux data to produce an augmented complete tomographic projection set; and
   (iv) reconstruct a tomographic image of the patient from the augmented complete tomographic projection set.

2. The combination radiation therapy and tomographic imaging machine of claim 1 wherein the low flux data comprises a complete tomographic projection set.

3. The combination radiation therapy and tomographic imaging machine of claim 1 wherein the low flux data comprises an incomplete tomographic projection set.

4. The combination radiation therapy and tomographic imaging machine of claim 1 wherein the modulator includes multiple leaves having open and closed positions to pass or occlude rays and wherein the low flux rays are obtained from leakage through the leaves.

5. The combination radiation therapy and tomographic imaging machine of claim 4 wherein the modulator is a set of leaves movable between closed and open states to occlude and pass rays, and wherein for each leaf, a proportion of time in the open state is controlled during intervals of axis angle according to the radiation treatment plan to produce the high flux incomplete tomographic projection set; and wherein the electronic computer executes the stored program to position the proportion of time in the open state after a beginning of each angular interval and wherein the low flux data is collected at the beginning of each angular interval.

6. The combination radiation therapy and tomographic imaging machine of claim 1 wherein the modulator includes multiple leaves having open and closed positions to pass or occlude rays and wherein the low flux rays are obtained by opening of leaves to pass rays not required by the radiation treatment plan.

7. The combination radiation therapy and tomographic imaging machine of claim 6 wherein the modulator is a set of binary actuated leaves movable between closed and open states to occlude and pass rays, and wherein for each leaf a proportion of time in the open state is controlled during intervals of axis angle according to the radiation treatment plan to produce the high flux incomplete tomographic projection set; and wherein the electronic computer executes the stored program to center the open state within each angular intervals and wherein the low flux data is collected at the center of each angular interval.

8. The combination radiation therapy and tomographic imaging machine of claim 7 wherein the modulator provides a set of controllable leaves operable for modulating rays, and wherein the electronic computer executes the stored program to optimize a pattern of operating the leaves to satisfy the radiation treatment plan given an opening of the leaves to generate the low flux data.

9. The combination radiation therapy and tomographic imaging machine of claim 1 wherein the radiation source provides a controlled emission of radiation and wherein the low flux rays are obtained by controlling the radiation source.

10. The combination radiation therapy and tomographic imaging machine of claim 1 wherein the electronic computer further executes the stored program to:

control the modulator to direct selected low flux rays at selected axis angles at the patient within the treatment volume according to a radiation treatment plan, the selected rays and angles comprising less than a tomographic projection set, to acquire a low flux incomplete tomographic projection set from the radiation detector; and combine the augmented tomographic projections set and the low flux incomplete tomographic projection set.

11. The combination radiation therapy and tomographic imaging machine of claim 1 wherein the electronic computer further operates to:

control the modulator to direct selected high flux rays at selected axis angles at the treatment volume without the patient according to a radiation treatment plan, the selected rays and angles comprising less than a tomographic projection set, to acquire a normalizing high flux incomplete tomographic projection set from the radiation detector;

direct low flux rays through the treatment volume without the patient to acquire normalizing low flux data from the radiation detector;

prior to combining the high flux incomplete tomographic projection set and the low flux data to produce an augmented complete tomographic projection set; normalizing the high flux incomplete tomographic projection set with the normalizing high flux incomplete tomographic projection, and normalizing the low flux data with the normalizing low flux data.

12. The combination radiation therapy and tomographic imaging machine of claim 11 wherein the data acquired from the radiation detector for reconstruction is obtained only at times when the beam is not being modulated.

13. The combination radiation therapy and tomographic imaging machine of claim 1 wherein the acquisition of the high flux incomplete tomographic projection set is interleaved with acquisition of the low flux data as the axis angle is changed.

14. The combination radiation therapy and tomographic imaging machine of claim 1 wherein the modulator is a set of actuated leaves movable between closed and open states to occlude and pass rays, and wherein for each leaf a proportion of time in the open state is controlled during intervals of axis angle according to the radiation treatment plan to produce the high flux incomplete tomographic projection set; and wherein the electronic computer executes the stored program to position the open state a predetermined time after a beginning of each angular interval and wherein the low flux data is collected at the beginning of each angular interval.

15. A combination radiation therapy and tomographic imaging machine comprising:

a megavoltage radiation source directing a radiation beam formed of rays directed generally along an axis;

a gantry holding the radiation source to rotate the angle of the axis about a treatment volume;

a radiation detector positioned on the gantry across the treatment volume opposite the radiation source to receive and measure radiation of the rays to provide data of a projection;

a modulator modulating the flux of the rays passing through the treatment volume; and an electronic computer executing a stored program to:
  (i) control the modulator to direct selected high flux rays at selected axis angles at the patient within the treatment volume according to a radiation treatment plan, the selected rays and angles comprising less than a tomographic projection set, to acquire a high flux incomplete tomographic projection set from the radiation detector;
  (ii) control the modulator to close the leaves to direct low flux rays at the patient within the treatment volume to acquire low flux data from the radiation detector;
  (iii) combine the high flux incomplete tomographic projection set and the low flux data to produce an augmented complete tomographic projection set; and
  (iv) reconstruct a tomographic image of the patient from the augmented complete tomographic projection set.

16. The combination radiation therapy and tomographic imaging machine of claim 15 wherein a proportion of time that each leaf is in the open state is controlled during intervals of axis angle according to the radiation treatment plan to produce the high flux incomplete tomographic projection set; and wherein the electronic computer executes the stored program to position the open state after a beginning of each angular interval and wherein the low flux data is collected at the beginning of each angular interval.

17. A combination radiation therapy and tomographic imaging machine comprising:

a megavoltage radiation source directing a radiation beam formed of rays directed generally along an axis;

a gantry holding the radiation source to rotate the angle of the axis about a treatment volume;

a radiation detector positioned on the gantry across the treatment volume opposite the radiation source to receive and measure radiation of the rays to provide data of a projection;

a modulator providing a set of binary actuated leaves movable between closed and open states to occlude and pass rays, and wherein for each leaf a proportion of time in the open state may be controlled during intervals of axis angle;

a means for determining windowed times during which the leaves of the modulator are substantially stationary for collecting tomographic data from the radiation detector; and an electronic computer programmed for reconstructing a tomographic image of the patient from the tomographic data collected during the windowed times.

* * * * *